United States Patent
Ohmachi et al.

(10) Patent No.: US 10,603,362 B2
(45) Date of Patent: *Mar. 31, 2020

(54) BEVERAGE, AND METHOD OF PRODUCING THE SAME

(71) Applicant: MEGMILK SNOW BRAND CO., LTD., Hokkaido (JP)

(72) Inventors: Aiko Ohmachi, Saitama (JP); Hiroaki Matsuyama, Saitama (JP); Yoshikazu Morita, Saitama (JP); Yuko Ishida, Saitama (JP); Takayuki Nara, Saitama (JP); Ken Kato, Saitama (JP); Atsushi Serizawa, Sapporo (JP); Hiroshi Ueno, Saitama (JP); Hiroshi Urazono, Saitama (JP)

(73) Assignee: MEGMILK SNOW BRAND CO., LTD., Hokkaido (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/640,977

(22) Filed: Jul. 3, 2017

(65) Prior Publication Data

US 2017/0296632 A1   Oct. 19, 2017

Related U.S. Application Data

(62) Division of application No. 14/418,261, filed as application No. PCT/JP2012/069394 on Jul. 31, 2012, now abandoned.

(51) Int. Cl.

| | | |
|---|---|---|
| *A61K 38/17* | (2006.01) | |
| *A61K 38/46* | (2006.01) | |
| *A61K 38/44* | (2006.01) | |
| *A23C 9/146* | (2006.01) | |
| *A23L 2/52* | (2006.01) | |
| *A23C 9/15* | (2006.01) | |
| *A23C 9/152* | (2006.01) | |

(52) U.S. Cl.
CPC .......... *A61K 38/465* (2013.01); *A23C 9/1465* (2013.01); *A23C 9/1512* (2013.01); *A23C 9/1526* (2013.01); *A23L 2/52* (2013.01); *A61K 38/44* (2013.01); *A23V 2002/00* (2013.01); *C12Y 111/01007* (2013.01); *C12Y 301/27* (2013.01)

(58) Field of Classification Search
CPC ................................................ A61K 38/1709
See application file for complete search history.

(56) References Cited

U.S. PATENT DOCUMENTS

| | | | |
|---|---|---|---|
| 5,976,597 | A | 2/1999 | Takada et al. |
| 5,932,259 | A | 8/1999 | Kato et al. |
| 8,551,547 | B2 | 3/2013 | Brown et al. |
| 8,647,619 | B2 | 2/2014 | Motouri et al. |
| 2006/0289345 | A1 | 10/2006 | Motouri et al. |
| 2010/0136172 | A1 | 6/2010 | Brown et al. |
| 2010/0209412 | A1 | 8/2010 | Motouri et al. |
| 2011/0008361 | A1 | 1/2011 | Bragger |
| 2011/0151016 | A1 | 6/2011 | McDonagh et al. |
| 2011/0262422 | A1 | 10/2011 | Cocks et al. |
| 2012/0040908 | A1 | 2/2012 | Kido et al. |
| 2015/0182557 | A1 | 7/2015 | Ohmachi et al. |
| 2015/0224178 | A1 | 8/2015 | Ohmachi et al. |
| 2015/0297690 | A1 | 10/2015 | Ohmachi et al. |
| 2015/0343029 | A1 | 12/2015 | Ohmachi et al. |

FOREIGN PATENT DOCUMENTS

| | | |
|---|---|---|
| JP | H06-135996 A | 5/1994 |
| JP | 8-151331 | 6/1996 |
| JP | H08-165249 A | 6/1996 |
| JP | H09-191858 A | 7/1997 |
| JP | 10-007585 | 1/1998 |
| JP | 2004-238320 | 8/2004 |
| JP | 2005-060321 | 3/2005 |
| JP | 2005-104900 | 4/2005 |
| JP | 2008-543850 | 12/2008 |
| JP | 2009-215301 | 9/2009 |
| JP | 2010-508827 A | 3/2010 |
| JP | 2011-519960 | 7/2011 |
| WO | 2009/137879 | 11/2009 |
| WO | 2009137881 A1 | 11/2009 |
| WO | 2010/028432 | 3/2010 |
| WO | 2010/058679 A | 5/2010 |

OTHER PUBLICATIONS

Vishal Tripathi and Bhavana Vashishtha, "Bioactive Compounds of the Colostrum and Its Application," (2006) Food Rev. Int'l, 22(3):225-244.
Ming Du, et al. "Protective effects of bovine colostrum acid proteins on bone loss of ovariectomized rats and the ingredients identification," (2011) Molecular Nutr. Food Res. 55:220-228.
Brief Communication issued by the European Patent Office in counterpart Application No. 12882174.1 dated Sep. 7, 2018.
Summons to Attend Oral Proceedings issued by the European Patent Office in counterpart Application No. 12882174.1 dated Jul. 17, 2018.
International search report issued with respect to application No. PCT/JP2012/069394, dated Sep. 11, 2012.
Y. Morita et al., "Purification and identification of lactoperoxidase in milk basic proteins as an inhibitor of osteoclastogenesis", Journal of Dairy Science, 2011, vol. 94, No. 5, pp. 2270-2279.
International preliminary report on patentability issued with respect to application No. PCT/JP2012/069394, dated Feb. 3, 2015.
Morita et al., "Identification of Angiogenin as the Osteoclastic Bone Resorption-Inhibitory Factor in Bovine Milk", *Bone*, vol. 42, No. 2, pp. 380-387, 2008.
Extended European Search Report issued in EP Patent Application No. 12882174.1, dated Jan. 5, 2016.
Partial English-language translation of JP 2005-060321 (Mar. 10, 2005).

(Continued)

*Primary Examiner* — Rosanne Kosson

(74) *Attorney, Agent, or Firm* — Greenbaum & Bernstein, P.L.C.

(57) ABSTRACT

The invention relates to a drink includes angiogenin and/or angiogenin hydrolysate in an amount of more than 0.8 mg/100 ml and not more than 150 mg/100 ml, and lactoperoxidase and/or lactoperoxidase hydrolysate in the mass ratio to the angiogenin and/or angiogenin hydrolysate of 0.3 to 23.

10 Claims, No Drawings

(56) References Cited

OTHER PUBLICATIONS

Komolova et al., "Milk Angiogenin"; Applied Biochemistry and Microbiology; vol. 38, No. 3, Jan. 1, 2002; pp. 199-204.
Losnedahl et al., "Antimicorbial Factors in Milk-Diary Cattle", Illinois Livestock Trail , Aug. 5, 1998, pp. 1-10.
European Office Action issued in Counterpart Patent Appl. No. 12 882 174.1, dated Jun. 19, 2017.
Japanese Office Action with English Translation in respect to Japanese Application No. 2017-035647, dated Mar. 7, 2018.

BEVERAGE, AND METHOD OF PRODUCING THE SAME

This application is a Divisional of U.S. patent application Ser. No. 14/418,261, which is the National Stage of International Patent Application No. PCT/JP2012/069394, filed Jul. 31, 2012. The disclosures of each of application Ser. No. 14/418,271 and PCT/JP2012/069394 are expressly incorporated by reference herein in their entireties.

TECHNICAL FIELD

This invention relates to a beverage and a method of producing the same. The drink includes a specific milk component, and may be useful for prevention and treatment of various bone diseases such as osteoporosis, fracture, rheumatism, and arthritis.

BACKGROUND ART

In recent years, various bone diseases, such as osteoporosis, fracture, and backache have increased on a global basis along with aging of society and the like, and have become a serious social problem. These diseases are caused by insufficient calcium intake, depression of calcium absorption ability, hormone imbalance after menopause, and the like. It is considered that increase the body bone mass as much as possible by activating the osteoblast and bone formation from the early stage of life, and increase the maximum bone mass and the bone strength (bone density+ bone quality) is effective in preventing various bone diseases, such as osteoporosis, fracture, and backache. Note that the term "bone quality" refers to the bone microstructure, metabolic turnover, microfracture, and calcification. It is thought that various bone diseases, such as osteoporosis, fracture, and backache may be prevented by suppressing osteoclastic bone resorption. Bones are always repeatedly resorbed and formed in a balanced manner (remodeling). However, various bone diseases, such as osteoporosis, fracture, and backache may occur when bone resorption exceeds bone formation due to a change in hormone balance after menopause, and the like. Therefore, bones can be strengthened by suppressing osteoclastic bone resorption and maintaining the bone strength at a constant level.

In view of the above situation, a drug, food, drink, feed, or the like, in which a calcium salt, such as calcium carbonate, calcium phosphate, or calcium lactate or a natural calcium product, such as whey calcium, bovine bone powder, or eggshell is added individually, has been taken in order to strengthen bones. A drug, food, drink, feed, or the like that contains such a calcium product together with a substance having a calcium absorption-promoting effect, such as casein phosphopeptide or oligosaccharide has also been used to strengthen bones. However, the calcium absorption rate is 50% or less when a food or drink that contains a calcium salt or a natural calcium product is taken, and the large part of the calcium taken may be discharged from the body without being absorbed. Moreover, even if calcium is absorbed into the body, it does not necessarily exhibit the bone metabolism-improving effect or a bone-strengthening effect, since the affinity to bones may differ according to its form or the type of nutritional ingredient taken together. An estrogen product, an active vitamin $D_3$ product, a vitamin $K_2$ product, a bisphosphonate product, a calcitonin product, and the like have been known as a drug for treating osteoporosis or strengthening hones, and new drugs such as an anti-RANKL antibody have been also developed. However, these drugs may have side effects such as buzzing in the ear, a headache, or loss of appetite. Moreover, the above substances are in a situation that they cannot be added to a food or drink at present from the viewpoint of safety, cost, and the like. Therefore, in light of the nature of various bone diseases, such as osteoporosis, fracture, and backache, development of such a food or chink that can be taken orally for a long time, increases the bone strength by promoting bone formation and suppressing bone resorption, and may be expected to have the effect of preventing or treating the various bone diseases has been desired.

PRIOR-ART DOCUMENT

Patent Document

[Patent Document 1] JP-A-H08-151331
[Patent Document 2] JP-A-H10-7585
[Patent Document 3] JP-A-2004-238320
[Patent Document 4] JP-A-2005-60321

SUMMARY OF THE INVENTION

Problems to be Solved by the Invention

The invention relates to provide a drink that may be useful for prevention and treatment of various bone diseases such as osteoporosis, fracture, rheumatism, and arthritis.

Means for Solving the Problems

The present inventors have found that the bone density can be effectively increased by ingesting a drink that includes angiogenin and/or angiogenin hydrolysate, and includes lactoperoxidase and/or lactoperoxidase hydrolysate in a specific mass ratio with respect to angiogenin and/or angiogenin hydrolysate. This finding has led to the completion of the invention.

Specifically, the invention includes following aspects:

(1) A drink including angiogenin and/or angiogenin hydrolysate in an amount of more than 0.8 mg/100 nil and not more than 150 mg/100 ml and lactoperoxidase and/or lactoperoxidase hydrolysate in the mass ratio to the angiogenin and/or angiogenin hydrolysate of 0.3 to 23.

(2) A method of preventing bone diseases including ingesting the drink according to (1) in an amount of 200 ml/day or more.

(3) A method of producing the drink according to (1), including mixing angiogenin and/or angiogenin hydrolysate and lactoperoxidase and/or lactoperoxidase hydrolysate with a drink raw material, and sterilizing the obtained mixture.

(4) A method of producing the drink according to (1), including adding angiogenin and/or angiogenin hydrolysate and lactoperoxidase and/or lactoperoxidase hydrolysate to a sterilized drink raw material.

DETAILED DESCRIPTION

Effects of the Invention

The drink of the invention exhibits a bone-strengthening effect, and may be useful for prevention and treatment of various bone diseases such as osteoporosis, fracture, rheumatism, and arthritis.

EMBODIMENTS FOR CARRYING OUT THE INVENTION

A drink of the invention is characterized in that the drink includes angiogenin and/or angiogenin hydrolysate in a specific amount, and further includes lactoperoxidase and/or lactoperoxidase hydrolysate in a specific mass ratio with respect to angiogenin and/or angiogenin hydrolysate.

Cow milk generally contains angiogenin and/or angiogenin hydrolysate in an amount of about 0.2 to 0.8 mg/100 ml, and lactoperoxidase and/or lactoperoxidase hydrolysate in an amount of about 1.5 to 6.0 mg/100 ml.

In contrast, the drink of the invention is added with angiogenin and/or angiogenin hydrolysate and lactoperoxidase and/or lactoperoxidase hydrolysate, and the drink contains angiogenin and/or angiogenin hydrolysate in an amount of more than 0.8 mg/100 ml and not more than 150 mg/100 ml, and lactoperoxidase and/or lactoperoxidase hydrolysate in a mass ratio with respect to angiogenin and/or angiogenin hydrolysate of 0.3 to 23.

A fraction containing angiogenin and/or angiogenin hydrolysate that is prepared from milk of a mammal, such as human, cow, buffalo, goat, or sheep, a fraction containing lactoperoxidase and/or lactoperoxidase hydrolysate that is prepared from milk of a mammal, such as human, cow, buffalo, goat, or sheep, a fraction containing angiogenin and/or angiogenin hydrolysate that is produced by a genetic engineering, a fraction containing lactoperoxidase and/or lactoperoxidase hydrolysate that is produced by a genetic engineering, angiogenin and/or angiogenin hydrolysate purified from blood or an organ, lactoperoxidase and/or lactoperoxidase hydrolysate purified from blood or an organ, or the like may be used as the angiogenin and/or angiogenin hydrolysate and the lactoperoxidase and/or lactoperoxidase hydrolysate included in the drink of the invention. A commercially available purified angiogenin or lactoperoxidase reagent may also be used.

The drink of the invention may include angiogenin hydrolysate or lactoperoxidase hydrolysate obtained by digesting a fraction containing angiogenin, an angiogenin reagent, a fraction containing lactoperoxidase, a lactoperoxidase reagent, or the like using one or more proteases.

The drink of the invention may include a protein material prepared by extracting a fraction containing angiogenin and/or angiogenin hydrolysate and lactoperoxidase and/or lactoperoxidase hydrolysate directly from milk or a material derived from milk, such as skim milk or whey. Such a protein material may be prepared as follows, for example. Specifically, milk or a material derived from milk is brought into contact with a cation-exchange resin, and milk-derived proteins adsorbed on the resin is eluted at a salt concentration of 0.1 to 2.0 M, desalted and concentrated using a reverse osmosis membrane, an electrodialysis membrane, an ultrafiltration membrane, a microfiltration membrane, or the like, and optionally subjected to proteolysis to a molecular weight of 8000 or less using a protease, such as trypsin, pancreatin, chymotrypsin, pepsin, papain, kallikrein, cathepsin, thermolysin, or V8 protease. When subjecting to proteolysis using a protease, the lower limit of the molecular weight is preferably 500 or more. The protein material thus obtained may be dried by freeze-drying, spray drying, or the like, and the dried product may be added in the drink.

The drink of the invention is produced by adding angiogenin and/or angiogenin hydrolysate, and lactoperoxidase and/or lactoperoxidase hydrolysate and a protein material that contains angiogenin and/or angiogenin hydrolysate and lactoperoxidase and/or lactoperoxidase hydrolysate, or the like to a drink raw material so that the drink includes angiogenin and/or angiogenin hydrolysate in an amount of more than 0.8 mg/100 ml and not more than 150 mg/100 ml, and includes lactoperoxidase and/or lactoperoxidase hydrolysate in a mass ratio with respect to angiogenin and/or angiogenin hydrolysate of 0.3 to 23.

As shown in the test examples described below, when the drink includes angiogenin and/or angiogenin hydrolysate and lactoperoxidase and/or lactoperoxidase hydrolysate as described above, the bone-strengthening effect can be obtained more effectively than the case of ingesting angiogenin and/or angiogenin hydrolysate or lactoperoxidase and/or lactoperoxidase hydrolysate separately.

The drink of the invention may be produced in the usual manner as long as the drink includes the angiogenin and/or angiogenin hydrolysate and lactoperoxidase and/or lactoperoxidase hydrolysate in specific amounts, respectively. For example, the drink of the invention is produced by adding angiogenin and/or angiogenin hydrolysate to a drink raw material, such as a material derived from milk so that the drink includes angiogenin and/or angiogenin hydrolysate in a specific amount, and adding lactoperoxidase and/or lactoperoxidase hydrolysate to the mixture so that the mass ratio of lactoperoxidase and/or lactoperoxidase hydrolysate to angiogenin and/or angiogenin hydrolysate is within the specific range. Note that as the drink raw material, such as a material derived from milk, cow milk, concentrated skim milk, skim milk powder, whey, butter, cream, fermented milk, a dairy lactic acid bacteria beverage, a lactic acid bacteria beverage, or the like can be given, further a milk drink mixed thereof as appropriate, processed milk, composition-modified milk, low-fat milk, fat-free milk, or the like can be given, for example.

When adding angiogenin and/or angiogenin hydrolysate and lactoperoxidase and/or lactoperoxidase hydrolysate to a drink raw material, such as a material derived from milk, angiogenin and/or angiogenin hydrolysate and lactoperoxidase and/or lactoperoxidase hydrolysate may be added to either unsterilized drink raw material, or a sterilized drink raw material. When adding to an unsterilized drink raw material, sterilization may be conducted after the addition. In this instance, heat sterilization is preferable. For example, the drink raw material itself, or the drink raw material to which angiogenin and/or angiogenin hydrolysate and lactoperoxidase and/or lactoperoxidase hydrolysate are added, may be heated to 70° C., homogenized using a homogenizer at a pressure of 15 MPa, sterilized at 130° C. for 2 seconds, and cooled to 5° C. When sterilizing a mixture prepared by adding angiogenin and/or angiogenin hydrolysate and lactoperoxidase and/or lactoperoxidase hydrolysate to a drink raw material, it is preferable to sterilize at 130° C. for 2 seconds or less.

It may be possible that the drink of the invention may be added with a raw material or the like that is commonly used for a food or drink, such as a saccharide, a lipid, a protein, a vitamin, a mineral, or a flavor, in addition to angiogenin and/or angiogenin hydrolysate, lactoperoxidase and/or lactoperoxidase hydrolysate, other than the above drink raw material, and may also be added with another bone-strengthening component such as calcium, vitamin D, vitamin K, or isoflavone.

The drink of the invention can strengthen bones when taken orally in an amount of 200 ml or more per kg of body weight, as shown in the animal experiments described below. Since the intake for the experiment animal corresponds to the intake for adults in terms of blood drug concentration (see Mitsuyoshi Nakajima (1993), "*Yakkou Hyoka* Vol. 8", Hirokawa-Shoten Ltd., pp. 2-18), it is expected that bones can be strengthened, and especially various bone diseases, such as osteoporosis, fracture, rheumatism, and arthritis can be prevented or treated by ingesting the drink of the invention in an amount of 200 ml/day or more per adult.

The invention is further described below in more detail by way of reference examples, examples, and test examples. Note that the following examples are intended for illustration purposes only, and should not be construed as limiting the invention.

Reference Example 1

Preparation (1) of Angiogenin Fraction

A column filled with 30 kg of cation-exchange resin (Sulfonated Chitopearl; manufactured by Fuji Spinning Co., Ltd.) was thoroughly washed with deionized water, and 1000 liters of unpasteurized skim milk (pH 6.7) was then applied to the column. After thoroughly washed the column with deionized water, the absorbed protein was eluted with a linear gradient of 0.1 to 2.0 M sodium chloride. The eluted fraction containing angiogenin was fractionated using an S-Sepharose cation-exchange chromatography (manufactured by Amersham Bioscientific), and the resulted angiogenin-containing fraction was heat-treated at 90° C. for 10 minutes, and centrifuged to remove a precipitate. The angiogenin-containing fraction was further subjected to gel filtration chromatography (column: Superose 12). The eluate obtained was desalted using a reverse osmosis membrane, and the desalted eluate was freeze-dried to obtain 16.5 g of an angiogenin fraction having an angiogenin purity of 90%. These successive operations were repeated 30 times.

Reference Example 2

Preparation (2) of Angiogenin Fraction

A column filled with 10 kg of Heparin Sepharose (manufactured by GE Healthcare) was thoroughly washed with deionized water, and 500 liters of unpasteurized skim milk (pH 6.7) was then applied to the column. After thoroughly washing the column with a 0.5 M sodium chloride solution, the column was eluted with a 1.5 M sodium chloride solution. The eluate was desalted using a reverse osmosis membrane, and the desalted eluate was freeze-dried to obtain 18 g of an angiogenin fraction having an angiogenin purity of 5%. The above successive operations were repeated 50 times.

Reference Example 3

Preparation of Lactoperoxidase Fraction

A column (diameter: 5 cm, height: 30 cm) filled with 600 g of cation-exchange resin (sulfonated Chitopearl; manufactured by Fuji Spinning Co., Ltd.) was thoroughly washed with deionized water, and 360 liters of unpasteurized skim milk (pH 6.7) was applied to the column at a flow rate of 25 ml/min. After thoroughly washing the column with deionized water, the absorbed protein was eluted with a 0.02 M carbonate buffer (pH 7.0) containing 2.0 M sodium chloride. The eluted fraction containing lactoperoxidase was adsorbed on an S-Sepharose FF column (manufactured by Amersham Bioscientific), and the column was thoroughly washed with deionized water. After equilibration with a 10 mM phosphate buffer (pH 7.0), the adsorbed fraction was eluted with a linear gradient of 0 to 2.0 M sodium chloride to collect a fraction containing lactoperoxidase. The fraction was subjected to gel filtration chromatography using a HiLoad 16/60 Superdex 75 pg (manufactured by Amersham Bioscientific). The eluate obtained was desalted using a reverse osmosis membrane, and freeze-dried to obtain 27 g of a lactoperoxidase fraction having a lactoperoxidase purity of 90%. These successive operations were repeated 25 times.

Measurement of Angiogenin and Lactoperoxidase Contained in Drink

The content of angiogenin, angiogenin hydrolysate, lactoperoxidase and lactoperoxidase hydrolysate in the drink was measured according to the method described in JP-A-2008-164511 with modification. Specifically, 106 µl of the drink was added to 5 ml of ultrapure water, and a 1/1000-equivalent amount of formic acid was added to the mixture to prepare a sample solution. Ten microliter (10 µl) of the sample solution was dried up, and dissolved in 20 µl of 0.1 M ammonium bicarbonate containing 8 M urea and 1 mM tris(carboxyethyl)phosphine (TCEP). The solution was heated at 56° C. for 30 minutes. After returning the solution to room temperature, 5 µl of 100 mM iodoacetamide solution was added to the solution, and the mixture was reacted for 30 minutes in the dark. After the addition of 54 µl of ultrapure water, 10 µl of 0.1 µg/ml trypsin and 10 µl of 0.1 µg/ml Lysyl Endopeptidase were added to the mixture. The mixture was reacted at 37° C. for 16 hours. The reaction was then terminated by adding 3 µl of formic acid and used as the sample peptide solution for measurement. The sample solution was diluted 6-fold with 10 fmol/µl internal standard peptide solution containing 0.1% formic acid, 0.02% trifluoroacetic acid (TFA), and 2% acetonitril, and 2.5 µl of the diluted solution was subjected to LC/MS/MS analysis.

The peptides were separated by gradient elution using an HPLC system. More specifically, the peptides were separated using a column (MAGIC C18, 0.2 mm (ID)×50 mm) equipped with a 5 µl-peptide trap on a MAGIC 2002 HPLC system at a flow rate of 2 µl/min. A solution A (2% acetonitrile-0.05% formic acid) and a solution B (90% acetonitrile-0.05% formic acid) were used as eluant for HPLC. Gradient elution was conducted under the elution condition from 2 to 65% using the solution B over 20 minutes.

As object ions for measuring lactoperoxidase, parent ion was $NH_2$-IHGFDLAAINLQR-COOH (m/z 734.4), and the MS/MS target ion was $NH_2$-IHGFDLA-COOH (m/z 754.4). As object ions for measuring angiogenin, parent ion was $NH_2$-YIHFLTQHYDAK-COOH (m/z 768.8), and the MS/MS target ion was $NH_2$-FLTQHYDAK-COOH (m/z 1122.8). Regarding the internal standard peptide parent ion was $NH_2$-ETTVFENLPEK-COOH (wherein, P was labeled with $^{13}C$ and $^{15}N$) (ink 656.9), and the MS/MS target ion was $NH_2$-FENLPEK-COOH (wherein, P was labeled with $^{13}C$ and $^{15}N$) (m/z 882.4).

A system "LCQ Advantage" was used for MS. The peak area of each protein was calculated from the resulting chromatogram, and the concentration was calculated from the ratio with respect to the internal standard peptide.

Example 1

Three hundred and thirty milligrams (330 mg) of the angiogenin fraction obtained in Reference Example 1 and 90 mg of the lactoperoxidase fraction obtained in Reference Example 3 were mixed with 200 ml of cow milk. The mixture was sterilized at 130° C. for 2 seconds, and cooled to 10° C. to obtain a drink (example product 1). The resulting drink contained angiogenin and/or angiogenin hydrolysate in an amount of 150 mg/100 ml, and the mass ratio of lactoperoxidase and/or lactoperoxidase hydrolysate to angiogenin and/or angiogenin hydrolysate in the drink was 0.3.

Example 2

Twenty four milligrams (24 mg) of the angiogenin fraction obtained in Reference Example 2 and 30 mg of the lactoperoxidase fraction obtained in Reference Example 3 were mixed with 200 ml of cow milk. The mixture was sterilized at 130° C. for 2 seconds, and cooled to 10° C. to obtain a drink (example product 2). The resulting drink contained angiogenin and/or angiogenin hydrolysate in an amount of 0.81 mg/100 ml, and the mass ratio of lactoperoxidase and/or lactoperoxidase hydrolysate to angiogenin and/or angiogenin hydrolysate in the drink was 23.

Example 3

Twenty four milligrams (24 mg) of the angiogenin fraction obtained in Reference Example 1 and 30 mg of the lactoperoxidase fraction obtained in Reference Example 3 were mixed with 200 ml of cow milk. The mixture was sterilized at 130° C. for 2 seconds, and cooled to 10° C. to obtain a drink (example product 3). The resulting drink contained angiogenin and/or angiogenin hydrolysate in an amount of 11 mg/100 ml, and the mass ratio of lactoperoxidase and/or lactoperoxidase hydrolysate to angiogenin and/or angiogenin hydrolysate in the drink was 1.7.

Comparative Example 1

Twenty milligrams (20 mg) of the angiogenin fraction obtained in Reference Example 2 and 34 mg of the lactoperoxidase fraction obtained in Reference Example 3 were mixed with 200 ml of cow milk. The mixture was sterilized at 130° C. for 2 seconds, and cooled to 10° C. to obtain a drink (comparative example product 1). The resulting drink contained angiogenin and/or angiogenin hydrolysate in an amount of 0.7 mg/100 ml, and the mass ratio of lactoperoxidase and/or lactoperoxidase hydrolysate to angiogenin and/or angiogenin hydrolysate in the drink was 29.

Comparative Example 2

Three hundred and sixty milligrams (360 mg) of the angiogenin fraction obtained in Reference Example 1 and 60 mg of the lactoperoxidase fraction obtained in Reference Example 3 were mixed with 200 ml of cow milk. The mixture was sterilized at 130° C. for 2 seconds, and cooled to 10° C. to obtain a drink (comparative example product 2). The resulting drink contained angiogenin and/or angiogenin hydrolysate in an amount of 162 mg/100 ml, and the mass ratio of lactoperoxidase and/or lactoperoxidase hydrolysate to angiogenin and/or angiogenin hydrolysate in the drink was 0.19.

Test Example 1

The bone-strengthening effects of the example products 1 to 3 and the comparative example products 1 and 2 were determined by animal experiments. C3H/HeJ mice (5 weeks old, male) were used for the animal experiments. After 1 week acclimation, the mice were divided into six groups (10 mice/group). The mice were orally administered each product of the example products 1 to 3 and the comparative example products 1 and 2 in an amount of 200 ml per 1 kg of mouse weight once a day for 2 weeks using a tube. The control group was not administrated any example products 1 to 3 and the comparative example products 1 and 2 were not administered. After completion of administration (second week), the bone density of the right tibia of each mouse was measured using a micro-CT (manufactured by Rigaku Corporation). The results are shown in Table 1. As shown in Table 1, the groups that were orally administered the example products 1 to 3 showed a significant increase in bone density compared with the control group and the comparative example groups that were orally administered the comparative example product 1 or 2.

TABLE 1

|  | Bone density (mg/cm$^3$) |
| --- | --- |
| Control group | 1239 ± 8 |
| Example product 1 | 1264 ± 12 |
| Example product 2 | 1271 ± 12 |
| Example product 3 | 1267 ± 13 |
| Comparative example product 1 | 1243 ± 6 |
| Comparative example product 2 | 1244 ± 6 |

Reference Example 4

A column (diameter: 4 cm, height: 30 cm) filled with 400 g of cation-exchange resin (Sulfonated Chitopearl; manufactured by Fuji Spinning Co., Ltd.) was thoroughly washed with deionized water, and 40 liters of unpasteurized skim milk (pH 6.7) was applied to the column at a flow rate of 25 ml/min. After thoroughly washing the column with deionized water, proteins adsorbed on the resin were eluted using a 0.02 M carbonate buffer (pH 7.0) containing 0.78 M sodium chloride. The eluate was desalted using a reverse osmosis membrane, and the desalted eluate was freeze-dried to obtain 18 g of a powdery protein material (reference example product 4).

Reference Example 5

Four grams (4 g) of protein material of the reference example product 4 was dissolved in 800 ml of water. After the addition of trypsin (manufactured by Sigma), which is a protease, so as to obtain the final concentration of 0.03 wt %, the mixture was subjected to enzymatic treatment at 37° C. for 8 hours. After inactivating the protease through heat-treatment at 90° C. for 5 minutes, the mixture was freeze-dried to obtain 3.0 g of a powdery protein material (reference example product 5).

Example 4

Forty milligrams (40 mg) of the reference example product 4 was mixed with 200 ml of sterilized cow milk to obtain a drink (example product 4). The resulting drink contained angiogenin and/or angiogenin hydrolysate in an amount of 1.2 mg/100 ml, and the mass ratio of lactoperoxidase and/or lactoperoxidase hydrolysate to angiogenin and/or angiogenin hydrolysate in the drink was 7.5.

Example 5

Forty milligrams (40 mg) of the reference example product 5 was mixed with 200 ml of sterilized cow milk to obtain a drink (example product 5): The resulting drink contained angiogenin and/or angiogenin hydrolysate in an amount of 1.15 mg/100 ml, and the mass ratio of lactoperoxidase and/or lactoperoxidase hydrolysate to angiogenin and/or angiogenin hydrolysate in the drink was 7.4.

Comparative Example 3

Fifteen milligrams (15 mg) of the reference example product 4 and 25 mg of the lactoperoxidase fraction obtained in Reference Example 3 were mixed with 200 ml of sterilized cow milk to obtain a drink (comparative example product 3). The resulting drink contained angiogenin and/or angiogenin hydrolysate in an amount of 0.7 mg/100 ml, and the mass ratio of lactoperoxidase and/or lactoperoxidase hydrolysate to angiogenin and/or angiogenin hydrolysate in the drink was 25.4

Test Example 2

The bone-strengthening effects of the example products 4 and 5 and the comparative example product 3 was determined by animal experiments. Forty SD female rats (51 weeks old) were used for the animal experiments. The rats were divided into five groups (8 rats/group). Four groups underwent ovariectomy, and the remaining one group sham surgery. After a 4-weekrecovery period, the ovariectomized rats were orally administered the example products 4 or 5 or the comparative example product 3 in an amount of 200 ml per 1 kg of rat weight daily in six divided dose for 16 weeks using a tube. The control group was not administrated any example products 4 and 5 and the comparative example product 3. After 4-week recovery period, the rats underwent sham surgery were fed for 16 weeks in the same manner as the control group. After completion of administration (sixteenth week), the bone density of the right tibia of each rat was measured using a micro-CT (manufactured by Rigaku Corporation).

The results are shown in Table 2. As shown in Table 2, the groups that were orally administered the example products 4 and 5 showed a significant increase in bone density as compared with the control group and the group that was orally administered the comparative example product 3. Moreover, the bone density approached that of the sham surgery group.

TABLE 2

| | Bone density (mg/cm$^3$) |
|---|---|
| Control group | 551 ± 11 |
| Sham surgery group | 602 ± 9 |
| Example product 4 | 595 ± 10 |
| Example product 5 | 596 ± 14 |
| Comparative example product 3 | 554 ± 13 |

The invention claimed is:

1. A method of increasing bone density comprising:
   administering to a subject in need of increased bone density,
   a drink comprising
      angiogenin and/or angiogenin hydrolysate in an amount of more than 0.8 mg/100 ml and not more than 150 mg/100 ml and
      lactoperoxidase and/or lactoperoxidase hydrolysate in the mass ratio to the angiogenin and/or angiogenin hydrolysate of 0.3:1 to 23:1
   in an amount of 200 ml/day or more.

2. A method of reducing the likelihood of at least one symptom of at least one bone disease comprising:
   administering to a subject diagnosed with at least one symptom of bone disease,
   a drink comprising
      angiogenin and/or angiogenin hydrolysate in an amount of more than 0.8 mg/100 ml and not more than 150 mg/100 ml and
      lactoperoxidase and/or lactoperoxidase hydrolysate in the mass ratio to the angiogenin and/or angiogenin hydrolysate of 0.3:1 to 23:1
   in an amount of 200 ml/day or more.

3. The method of reducing the likelihood of at least one symptom of at least one bone disease according to claim 2, wherein the symptom is a loss of bone density.

4. The method of reducing the likelihood of at least one symptom of at least one bone disease according to claim 2, wherein the subject is diagnosed with at least osteoporosis.

5. A method of reducing the likelihood of at least one symptom of at least one bone disease according to claim 2, wherein the subject is diagnosed with at least microfracture and/or fracture.

6. A method reducing the likelihood of at least one symptom of at least one bone disease according to claim 2, wherein the subject is diagnosed with at least rheumatism.

7. A method of reducing the likelihood of at least one symptom of at least one bone disease according to claim 2, wherein the subject is diagnosed with at least arthritis.

8. A method of reducing the likelihood of at least one symptom of at least one bone disease according to claim 1, wherein the subject is diagnosed with at least backache.

9. A method reducing the likelihood of at least one symptom of at least one bone disease according to claim 4, wherein the subject diagnosed with at least osteoporosis is female.

10. The method of increasing bone density according to claim 1, wherein the subject in need of increased bone density is male.

* * * * *

UNITED STATES PATENT AND TRADEMARK OFFICE
CERTIFICATE OF CORRECTION

PATENT NO. : 10,603,362 B2
APPLICATION NO. : 15/640977
DATED : March 31, 2020
INVENTOR(S) : Ohmachi et al.

Page 1 of 1

It is certified that error appears in the above-identified patent and that said Letters Patent is hereby corrected as shown below:

In the Claims

Column 10, Line 37 Claim 6, insert -- of -- after method;

Column 10, Line 45 Claim 9, insert -- of -- after method.

Signed and Sealed this
Twenty-ninth Day of December, 2020

Andrei Iancu
*Director of the United States Patent and Trademark Office*